United States Patent [19]

Nagamoto

[11] 4,373,392
[45] Feb. 15, 1983

[54] SENSOR CONTROL CIRCUIT

[75] Inventor: Shunichi Nagamoto, Nara, Japan

[73] Assignee: Matsushita Electric Industrial Co., Ltd., Osaka, Japan

[21] Appl. No.: 165,007

[22] Filed: Jul. 1, 1980

[30] Foreign Application Priority Data

Jul. 4, 1979 [JP] Japan .................. 54-84646

[51] Int. Cl.³ .................................. G01W 1/00
[52] U.S. Cl. .......................... 73/336.5; 324/65 R
[58] Field of Search .............. 73/73, 335, 336.5; 338/35; 324/65 R

[56] References Cited

U.S. PATENT DOCUMENTS 3,478,573 11/1969 King, Jr. .
3,553,576 1/1971 Petitjean et al. .
4,080,564 3/1978 Nitta et al. .
4,086,556 4/1978 Nitta et al. .

FOREIGN PATENT DOCUMENTS 13022 12/1979 European Pat. Off. .
974924 11/1964 United Kingdom .
1282993 7/1972 United Kingdom .
1353006 5/1974 United Kingdom .

*Primary Examiner*—James J. Gill
*Attorney, Agent, or Firm*—Wenderoth, Lind & Ponack

[57] ABSTRACT

A sensor control circuit for detecting water vapor, various gases, etc. The sensor control circuit includes a sensor element whose impedance varies according to the concentration of water vapor, gas or the like and further includes a heating element for heating said sensor element, the heating element being integrally disposed with the sensor element. The aforementioned integrated structure precludes entry of the electric signal applied to the heating element into the impedance detection signal of the sensor element, thus ensuring an accurate detection of the impedance of the sensor element.

7 Claims, 6 Drawing Figures

SENSOR CONTROL CIRCUIT

BACKGROUND OF THE INVENTION

For the purpose of automating cooking appliances, such as an electronic range, an electric oven, etc., there have already been developed a method in which the water vapor and various gases released from a food are detected by a sensor means and the heating temperature is accordingly controlled. The sensor means usually employed in this type of cooking appliance includes a heating element as disposed near the sensor element so as to vary the sensitivity of the sensor element or protect the sensor element against accumulation of dust from the ambient atmosphere and from vaporized oil, etc. from the food. A sensor means developed earlier includes a coil-shaped heater element 26 (see FIG. 3) around a sensor element 1 and the two elements are electrically separated from each other. Thus, as will be apparent from FIG. 3, the electric signal supplied to the coil for causing the coil heater 26 to generate heat does not exert any influence on the impedance detection signal of the sensor element 1 and, therefore, the impedance of sensor element 1 can be easily detected. However, despite the above-noted advantage, the sensor means of this type is disadvantageous in that because the coil heater 26 and sensor element 1 are disposed in a spaced-apart relationship, the heater 26 must be supplied with a relatively large electric power in order to heat the sensor element 1 and in addition, the heater 26 and sensor element 1 must be securely held in position in order to maintain their delicate spatial relationship.

To obviate the above-noted disadvantage, it might be contemplated to construct a sensor means having a high thermal efficiency by integrating a heating element and a sensor element as a single unit. However, it is quite likely that, in such an integrated setup, the electric signal applied to the heating element influences the impedance detection signal of the sensor element.

This invention provides a sensor control arranged such that the electric signal applied to the heating element does not influence the impedance detection signal of the sensor element.

SUMMARY OF THE INVENTION

A primary object of this invention is to provide a sensor control circuit which comprises, in an integral combination, a sensor element for detecting water vapor and various gases and a heating element, wherein one of two plate electrodes functions as a heating element and wherein a second power source is applied between said electrodes for detecting the impedance of the sensor element.

Another object of this invention is to provide a sensor control circuit in which said first and second power sources are electrically free from ground.

A further object of this invention is to provide a sensor control circuit arranged such that the impedance of the sensor element is detected between the point of connection of two substantially equivalent impedance elements connected in series between two lead wires extending from an electrode plate functioning as a heating element on the one hand and a lead wire extending from another electrode plate on the other hand.

BRIEF DESCRIPTION OF THE DRAWINGS

This invention will be further described with reference to the accompanying drawings, in which.

DESCRIPTION OF THE INVENTION

Figure 1A:
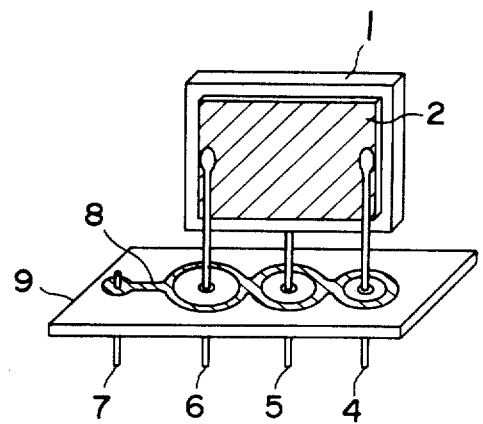
FIGS. 1a and 1b, respectively, show the exterior appearance of a sensor means according to this invention.
Figure 1B:
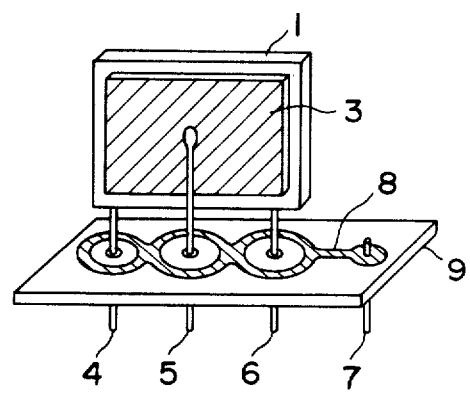

Referring to FIG. 1a and FIG. 1b, each of which is an exterior view of the sensor means according to this invention, a sensor element (1) which is made of a ceramic material such as, for example, magnesium spinel-rutile ($MgCrO_4$-$TiO_2$), is sandwiched between a first electrode plate (2) and a second electrode plate (3). The first and second electrodes (2) and (3) are each made, for example, of ruhenium oxide ($RuO_2$) and each has a predetermined resistance value. Lead wires (4) and (6) extend from said first electrode plate (2), and a lead wire (5) extends from said second electrode plate (3). The first electrode (2), in particular, functions as a heating element and generates heat when a voltage is applied between lead wires (4) and (6), whereby the sensor element (1) is heated. The reference numeral (7) denotes a lead wire for a guard electrode (8) which is disposed so as to surround the lead wires (4), (5) and (6); the reference numeral (9) indicates a base which may be advantageously made of alumina ($Al_2O_3$), to which lead wires (4), (5), (6) and (7) are rigidly secured and on which said guard electrode (8) is printed.

Figure 2A:
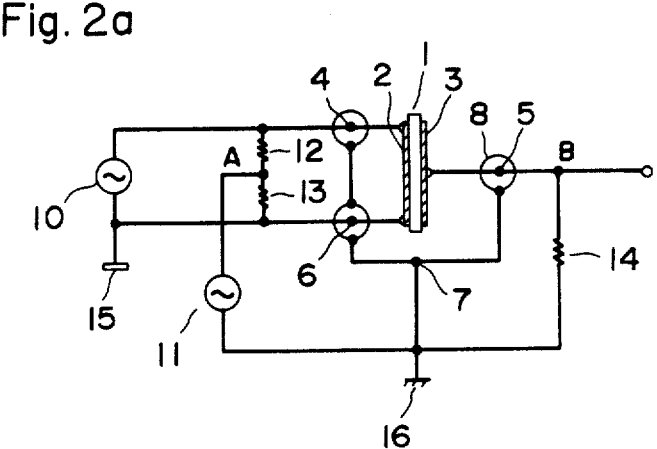
FIG. 2a shows a control circuit for said sensor means according to this invention.
Figure 2B:
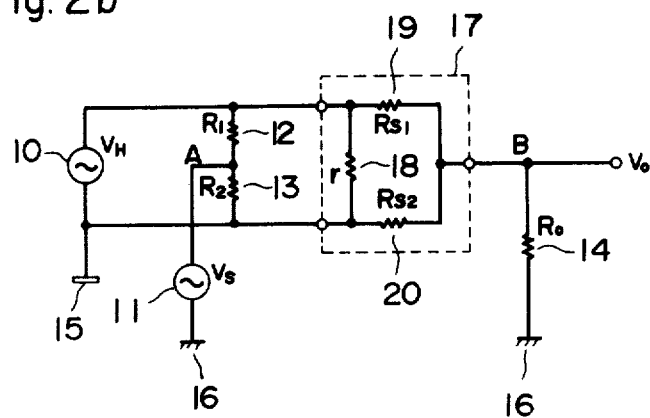
FIG. 2b is an equivalent circuit thereof.
Figure 2C:
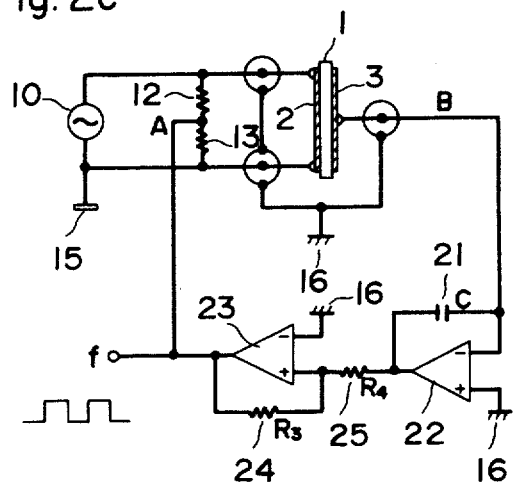
FIG. 2c shows another sensor control circuit according to this invention.
Figure 3:
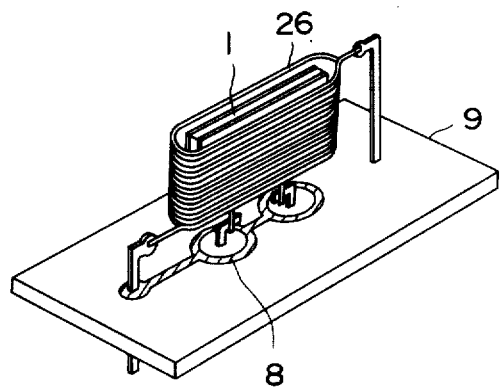
FIG. 3 is an exterior view showing the conventional sensor means.

The setup for controlling said sensor means will now be described with reference to FIGS. 2a to 2c. In FIG. 2a there is shown a first power source (10) for applying a voltage to said first electrode plate (2) and thereby causing it to generate heat. The first power source (10) is grounded at (15) which is referred to as a first ground. There is also shown a second power source (11); one end of the second power source is connected to a connection point A between resistors (12) and (13) and the other end thereof is connected to a second ground (16). The other ends of resistors (12) and (13) are connected to lead wires (4) and (6), respectively. There is further shown a resistor (14); one end of resistor (14) is connected to lead wire (5) at a connection point B and the other end thereof is connected to said second ground (16). FIG. 2b is an equivalent circuit diagram of FIG. 22 where the sensor circuit is conceived as indicated at 17. Thus, the reference numeral (18) denotes an equivalent resistance γ between the lead wires (4) and (6) of the first electrode plate (2). This resistance generates heat when supplied with energy from the first power source (10) and thereby heats said sensor element (1). The reference numerals (19) and (20) represent the equivalent resistances $R_{s1}$ and $R_{s2}$ of the sensor element, which vary according to the concentration of water vapor or gas. In the above-noted construction, the values $R_1$ and $R_2$ of resistors (12) and (13) may be made sufficiently small as compared with the equivalent resistances $R_{s1}$ and $R_{s2}$ of sensor element and the equivalent resistance γ of said first electrode plate (2) which inherently functions as an electrode and which assumes a sufficiently low value as compared with the equivalent resistances $R_{s1}$ and $R_{s2}$ of the sensor element. Therefore, the substantial equivalent resistance between connection points A and B may be regarded as a parallel resistance of equivalent resistances $R_{s1}$ and $R_{s2}$ of the sensor element and this may substantially be considered to be the impedance $R_s$ of the sensor element. Let it now be assumed that there is no influence from the first power source (10). Then, the output voltage obtainable across the resistor (14) is:

$$V_o = \frac{R_o}{R_o + R_s} \cdot V_s \qquad (1)$$

where $R_o$ is the resistance value of resistor (14). The impedance $R_s$ of sensor element (1) can thus be determined by measuring the voltage $V_s$ of the second power source (11) and the output voltage $V_o$.

While the above expression (1) is predicated on the assumption that there is no influence of said first power source (10), the actual requisite for no appearance of an electric signal due to $V_H$ in the output voltage $V_o$ is that the potential of connection point A and that of connection point B are exactly equal with respect to said first ground (15). Now, the values $R_1$ and $R_2$ of resistors (12) and (13), respectively, can be set to the same level and the equivalent resistances $R_{s1}$ and $R_{s2}$ of the sensor element are substantially equal in a homogeneous water vapor or gaseous atmosphere. Therefore, the above requisite is fulfilled and accordingly, there is no entry of the electric signal from said first power source (10) into the output voltage. FIG. 2c shows a sensor control means which converts the impedance between connection points A and B, i.e. the impedance of the sensor element, into the frequency of a pulse train. The oscillator consists of a capacitor (2), operational amplifiers (22), (23), resistors (24), (25) and the impedance between connection points A and B. The oscillation frequency f is represented by the expression:

$$f = \frac{R_1}{4CR_sR_2} \text{ (Hz)} \qquad (2)$$

where C is the capacity of the capacitor (21), $R_3$ and $R_4$ are the resistance values of resistors (24) and (25), respectively, and $R_s$ is the impedance between contact points A and B.

It will be apparent from the foregoing description that the sensor control circuit according to this invention provides for an improved accuracy of impedance detection in the field of art to which this invention pertains. It will also be apparent to those skilled in the art that many changes and modifications may be made in the described circuit and means without departing from the scope of the appended claims.

What is claimed is:

1. A sensor control circuit including a sensing device comprising a planar sensor element having two opposite major surfaces, first and second plate electrodes each having a predetermined exothermic resistance value and disposed on said two opposite major surfaces of said sensor element, two lead wires extending from said first plate electrode and connected to a power source whereby a current flowing through said lead wires and said first plate electrode causes said first plate electrode to generate heat, an additional lead wire extending from said second plate electrode, a pair of impedance elements connected in series between said two lead wires extending from said first plate electrode and a second power source interposed between the junction point of said pair of impedance elements and said additional lead wire extending from said second plate electrode and used for detecting the impedance of said sensor element.

2. A sensor control circuit as defined in claim 1, wherein said pair of impedance elements comprise a pair of resistors.

3. A sensor control circuit as defined in claim 1, wherein said pair of impedance elements comprise a pair of capacitors.

4. A sensor control circuit as defined in claims 1, 2 or 3, wherein said pair of impedance elements are equal in value, whereby the voltage between said junction point of said pair of impedance elements and said additional lead wire extending from said second plate electrode is independent of said first power source.

5. A sensor control circuit as defined in claim 1, wherein said sensor element comprises a ceramic material element.

6. A sensor control circuit as defined in claim 5, wherein said ceramic material is magnesium spinel-rutile.

7. A sensor control circuit as defined in claims 1, 5 or 6, wherein said plate electrodes comprise ruthenium oxide elements.

* * * * *